(12) United States Patent
Rudischhauser et al.

(10) Patent No.: US 6,425,857 B1
(45) Date of Patent: Jul. 30, 2002

(54) ENDOSCOPE, IN PARTICULAR VIDEO ENDOSCOPE

(75) Inventors: Jürgen Rudischhauser, Tuttlingen; Ulrich Kehr, Ostfildern, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/411,513

(22) Filed: Oct. 4, 1999

Related U.S. Application Data

(63) Continuation of application No. PCT/EP99/00453, filed on Oct. 8, 1998.

(30) Foreign Application Priority Data

Feb. 4, 1998 (DE) .......................... 198 04 234

(51) Int. Cl.[7] ................................. A61B 1/04
(52) U.S. Cl. ................... 600/112; 600/167; 600/133
(58) Field of Search .......................... 600/112, 167, 600/168, 173, 174, 109, 133; 348/65, 73, 75

(56) References Cited

U.S. PATENT DOCUMENTS

| | | | | |
|---|---|---|---|---|
| 4,902,129 A | * | 2/1990 | Siegmund et al. ............ | 348/65 |
| 4,930,861 A | * | 6/1990 | Okabe et al. ................. | 348/65 |
| 5,056,902 A | * | 10/1991 | Chinnock et al. ........... | 600/112 |
| 5,363,839 A | * | 11/1994 | Lankford ..................... | 600/112 |
| 5,836,867 A | * | 11/1998 | Speier et al. ................ | 600/112 |
| 5,899,851 A | * | 5/1999 | Koninckx ..................... | 600/117 |
| 5,978,161 A | * | 11/1999 | Lemke ......................... | 359/824 |
| 6,097,423 A | * | 8/2000 | Mattsson-Boze et al. ..... | 348/65 |
| 6,099,467 A | * | 8/2000 | Kehr et al. .................. | 600/112 |

* cited by examiner

Primary Examiner—John P. Leubecker
(74) Attorney, Agent, or Firm—St. Onge Steward Johnston & Reens LLC

(57) ABSTRACT

An endoscope, in particular a video endoscope, has an endoscope shaft at the distal end and a mount at the proximal end for attaching an optical imaging device, for example a video camera, and an endoscope housing between said endoscope shaft and said mount, said mount being rotatable relative to said endoscope shaft, via a rotary joint, about the longitudinal axis of said endoscope an optically imaging arrangement, which is at least partially positionally displaceable by way of an adjusting device for focusing the image transmission, moreover being received in said endoscope housing. Said endoscope housing is configured in continuously hermetically sealed fashion, and said rotary joint is arranged outside said endoscope housing.

20 Claims, 2 Drawing Sheets

ENDOSCOPE, IN PARTICULAR VIDEO ENDOSCOPE

CROSS REFERENCE OF PENDING APPLICATION

This application is a continuation of pending international application PCT/EP99/00453 filed Oct. 8, 1998.

BACKGROUND OF THE INVENTION

The present invention relates to an endoscope, in particular a video endoscope, having an endoscope shaft and having a mount for attaching an optical imaging device, for example a video camera, and having an endoscope housing between the endoscope shaft and the mount, the mount being rotatable relative to the endoscope shaft, via a rotary joint, about the longitudinal axis of the endoscope, an optically imaging arrangement, which is at least partially positionally displaceable by way of an adjusting device for focusing the image transmission, moreover being received in the endoscope housing.

An endoscope of this kind is known from U.S. Pat. No. 4,969,450.

In the field of endoscopy, increasing importance is being gained by those endoscopic systems in which the inspection field or surgical field in the human body that is observable through the endoscope is not observed directly by the operator through the endoscope eyepiece, but rather is made visible by way of an optical imaging device connected to the endoscope, for example a video camera, on an optical reproduction device, for example a monitor.

The endoscopes provided for this kind of use have, for this purpose, a mount at their proximal end for attaching the imaging device.

Various types of mounts, specifically bayonet or threaded mounts, are presently in use. These mounts are subject to standards in order to guarantee good compatibility between the available lens mounts, and the corresponding mounts of the imaging devices.

According to one DIN standard, for example, in the case of a camera lens mount referred to as a "C-mount," the flange distance, i.e. the distance between the camera's imaging plane and the surface at which the camera housing is mounted on the lens side mount, is defined.

Since the image plane is thus defined in the camera, focusing of the beam path in the lens must be performed.

If a C-mount of this kind is used in an endoscope for the video endoscope, it is therefore necessary to integrate the focusing system, i.e. the system by which the optical image is focused, into the endoscope. For this purpose, an endoscope housing, in which an optically imaging arrangement (generally a lens system) is received, is arranged between the endoscope shaft and the mount. For focusing purposes, the optically imaging arrangement is positionally displaceable via an adjusting device that can be controlled by the operator. The present invention is not, however, limited to a mount of this kind.

In such endoscopes for video endoscopy, it is also necessary for the video camera attached to the endoscope to be rotatable about the longitudinal axis of the endoscope relative to the endoscope shaft, so that in the case of a side-looking optical system, as large a region as possible of the surgical field can be optically detected, and different image locations can appear on the reproduction device. Since the video camera is joined nonrotatably to the mount, this means that the mount must be configured rotatably relative to the endoscope shaft.

In the endoscope known from U.S. Pat. No. 4,969,450 cited initially, the rotary joint necessary therefor is implemented by the fact that the endoscope housing between shaft and mount is configured in two parts, i.e. has an interruption, the mount being joined nonrotatably to the one housing part, and the endoscope shaft joined nonrotatably to the other housing part.

The endoscope housing is thus open at the joining point between the two housing parts; in the known endoscope, a seal for the interior space of the endoscope housing containing the optically imaging arrangement is effected by way of an O-ring between the two housing parts.

This kind of arrangement of the endoscope cited initially is, however, disadvantageous, since the O-ring seal cannot withstand sterilization conditions in an autoclave over the long term. In an autoclave, the endoscope is sterilized in pressurized and saturated steam at more than 120° C. Signs of wear on the O-ring can occur under these conditions even when a suitable material has been selected for the O-ring, so that following multiple sterilizations in the autoclave, the sealing effect can weaken and moisture can penetrate into the interior space of the endoscope housing; this either results in impairment of the optically imaging arrangement in the endoscope housing, for example due to fogging of the lenses, thus making the endoscope unusable, or at least entails increased maintenance effort.

It is thus the object of the invention to develop an endoscope of the kind cited initially in such a way that the endoscope can withstand the conditions in an autoclave over the long term.

SUMMARY OF THE INVENTION

According to the invention this object is achieved, in terms of the endoscope cited initially, in that the endoscope housing is configured in continuously hermetically sealed fashion, and that the rotary joint is arranged outside the endoscope housing at said mount.

In contrast to the split configuration of the endoscope housing of the known endoscope mentioned earlier, in the case of the endoscope according to the present invention the endoscope housing is configured in hermetically sealed fashion. "Hermetically sealed" means that no openings or interruptions sealed with sealing elements, such as joints, are provided in the endoscope housing. The interior space of the endoscope housing is thus completely hermetically sealed with respect to the exterior in terms of contamination, so that even when sterilization with steam in an autoclave occurs, no moisture at all can penetrate into the interior space of the endoscope housing. The hermetically sealed endoscope housing can be of one-piece or multi-piece configuration. In the case of a multi-piece configuration, the various pieces are joined in immovable and sealing fashion to one another, for example by welding, soldering, or the like, in order to meet the conditions of hermetic sealing tightness of the endoscope housing. The endoscope according to the present invention thus withstands the conditions in an autoclave over the long term, since no seals (such as O-rings) that can weaken over time are used. Provision is also made, according to the present invention, for the rotary joint necessary for rotatability of the mount relative to the endoscope shaft to be configured outside or beyond the sealed housing. In contrast to the known endoscope, the rotary joint is thus not integrated into the endoscope housing in the form of a two-part configuration thereof, thus achieving the advantage that the sealing tightness of the endoscope housing is not impaired by the rotary joint.

The underlying object of the invention is completely achieved in this fashion.

In a further embodiment, the rotary joint is arranged in the region of the proximal end of the endoscope housing.

The fact that the rotary joint is arranged at the proximal end of the endoscope housing yields the advantage that the image transmission systems arranged in the endoscope shaft and the endoscope housing can be configured nonrotatably with respect to one another, since only the mount, which usually does not itself contain any imaging system, is rotatable. Imaging defects possibly caused by rotation of the image transmission systems relative to one another are thereby advantageously prevented.

In a further preferred embodiment, the mount has at its distal end a sleeve that is arranged circumferentially and mounted rotatably on the endoscope housing.

This feature creates, in an advantageously mechanically simple manner, a rotary joint configured outside the sealed endoscope housing that in no way impairs the sealing tightness of the endoscope and that is easily operated by the operator; the advantage is additionally created that the endoscope is axially short, since the sleeve partially axially encloses the endoscope housing.

In a further preferred embodiment, the endoscope housing is joined nonrotatably to the endoscope shaft.

This feature has the advantage that when the camera is rotated relative to the endoscope shaft, the image transmission system contained in and fixed to the shaft, for example a relay lens system, is not rotated with respect to the optically imaging arrangement contained in the endoscope housing. Instead, these image transmission systems always assume the same rotational position with respect to one another. This means that image location deviations, which derive from tolerances of the image transmission system contained in the endoscope shaft and of the optically imaging arrangement contained in the endoscope housing and can be corrected by aligning these systems relative to one another once during assembly of the endoscope, do not occur again during rotation of the mount relative to the endoscope shaft while the endoscope is being used, so that re-alignment is no longer necessary. With the known endoscope cited initially, on the other hand, the endoscope shaft is rotatable relative to the endoscope housing and the optical arrangement contained therein, so that image location deviations and imaging errors can occur as the endoscope shaft is rotated relative to the housing.

In a further preferred embodiment, the adjusting device acts on the optically imaging arrangement from outside through the sealed endoscope housing.

Because of this feature, in contrast to the known endoscope cited initially, further openings in the endoscope housing, which must correspondingly be sealed externally using sealing means, are advantageously avoided. With the known endoscope, the adjusting device has a rotatable adjusting ring that is mechanically joined to the optically imaging arrangement through an opening in the endoscope housing. For the requisite sealing of the interior space of the endoscope housing, two O-rings are provided distally and proximally on the adjusting ring; these in turn are unsuitable for repeated sterilization of the endoscope in an autoclave. With the endoscope according to the present invention, however, provision is made for configuring the endoscope housing in hermetically sealed fashion and for allowing the adjusting device to act on the optically imaging arrangement from outside, thus eliminating seals using O-rings or the like, so that the autoclavability of the endoscope according to the present invention is further improved.

In a further preferred embodiment, the adjusting device acts on the optically imaging arrangement via a magnetic nonpositive engagement.

This feature has the advantage that the magnetic nonpositive engagement can effect a positional displacement of the optically imaging arrangement in the endoscope housing from outside without requiring, for that purpose, openings in the endoscope housing as in the case of a mechanical join. This does not, however, necessarily mean that the endoscope housing cannot be made of metal, since metals that do not substantially influence magnetic flux are available. The endoscope housing could, however, also be made of a nonmetallic material such as plastic or ceramic.

In a further preferred embodiment, the adjusting device has an adjusting ring that is arranged around the outer side of the endoscope housing and is rotatable relative to the endoscope shaft for positional displacement of at least a portion of the optically imaging arrangement.

With this embodiment of the adjusting device, the adjusting ring is rotated relative to the endoscope shaft in order to displace the optically imaging arrangement for focusing the beam path. When the adjusting ring is not held in place, it rotates along with the endoscope shaft by way of a corresponding frictionally engaged connection that can optionally be provided. This is advantageous when the endoscope shaft has a side-looking optical system and is rotated in the surgical field in order to observe a larger region of the surgical field.

In a further preferred embodiment, the adjusting device has an adjusting ring that is rotatable relative to the mount for positional displacement of at least a portion of the optically imaging arrangement.

This feature has the advantage that the endoscope makes possible one-handed operation, by the fact that for focusing, the operator can rotate the adjusting ring relative to the mount with two fingers of the hand with which he or she is holding the camera and can also rotate it relative to the endoscope shaft, without needing to hold the endoscope shaft in place.

In a further preferred embodiment, the adjusting device has at least one outer ring element, arranged rotatably around the outer side of the endoscope housing, that carries at least one magnet, and at least one rotatable inner ring element, arranged inside the endoscope housing, that also carries at least one magnet, such that a rotation of the outer ring element moves the inner ring element, and the movement of the inner ring element serves to positionally displace at least a portion of the optically imaging arrangement. The magnets can also be configured as multipole ring magnets magnetized on the inner or outer circumference.

This feature advantageously creates an adjusting device, in the manner of a magnetic coupling, that acts from outside, through the sealed endoscope housing and via a magnetic nonpositive engagement, on the optically imaging arrangement. In this context, the outer ring element is preferably joined to the aforementioned adjusting ring for operating the adjusting device.

It is further preferred in this context if the movement of the inner ring element is converted via a mechanical connection into an axial movement of at least a portion of the optically imaging arrangement.

This feature has the advantage that the aforementioned magnetic coupling can be configured in axially very compact fashion, since the inner and outer ring elements execute only a rotary movement, while the rotary movement of the inner ring element effects, via the mechanical connection (for example, threads), the axial movement of the optically imaging arrangement in order to focus the image.

In a further preferred arrangement, the adjusting device has two outer ring elements, arranged around the outer side of the endoscope housing, that each carry at least one magnet, and two inner ring elements, arranged inside the endoscope housing, that also each carry at least one magnet, such that a rotary movement of the outer ring elements moves the respective associated inner ring element, and such that a rotation of the one outer ring element relative to the other outer ring element effects a positional displacement of at least a portion of the optically imaging arrangement.

This embodiment of the adjusting device with two magnetic couplings rotatable relative to one another makes possible, in combination with the aforementioned adjusting ring that is rotatable relative to the mount for positional displacement of the optically imaging arrangement, an advantageous embodiment of the endoscope according to the present invention for one-handed operation.

It is preferred in this context if the one outer ring element is joined nonrotatably to the mount, and the other outer ring element is rotatable relative to the latter.

This feature has the advantage that for relative movement of the two magnetic couplings, only the one outer ring element needs to be rotated by way of an adjusting ring for focusing purposes, while the other ring element is joined nonrotatably to the mount. If the outer ring element that is rotatable relative to the mount is not rotated, it co-rotates upon rotation of the mount relative to the endoscope, so that no focusing takes place in that instance if it is not desired.

It is preferred in this context if the outer ring element that is not joined nonrotatably to the mount is joined in frictionally engaged fashion to the mount.

This feature yields the advantage that the outer ring element rotatable relative to the mount co-rotates with the latter if the mount is rotated relative to the endoscope shaft while the adjusting ring is not being held in place, without thereby causing focusing. The aforesaid frictionally engaged connection can be effected, for example, by way of an O-ring that is provided on the outer ring element or provided on an adjusting ring joined to the outer ring element.

In a further preferred embodiment, the optically imaging arrangement comprises an axially shiftable eyepiece lens arrangement of the endoscope and a stationary objective lens arrangement of the optical imaging device, and for focusing, the eyepiece lens arrangement is shifted by way of the adjusting device.

The advantage of this feature is that a smaller adjustment travel for the optical arrangement is required for focusing, since the eyepiece lens arrangement has a shorter focal length than the objective lens arrangement. A further advantage is the fact that if the eyepiece lens arrangement has an aperture, arranged in the intermediate image plane of the eyepiece, that is shiftable together with the eyepiece lens arrangement, this aperture is always sharply imaged. This creates the possibility of applying to the aperture a marking with reference to which the rotational position of the camera relative to the endoscope shaft (which is nonrotatable with respect to the aperture) can be determined.

It is further preferred if the optically imaging arrangement is arranged nonrotatably in the endoscope housing.

This feature, in conjunction with an endoscope shaft fastened nonrotatably to the endoscope housing, has the advantage that the image transmission system of the endoscope shaft always assumes the same rotational position with respect to the optically imaging arrangement, i.e. they cannot be rotated with respect to one another, so that image location deviations due to rotation of these two assemblies relative to one another are prevented.

In a further preferred embodiment, an aperture that has a marking for determining the rotational position of the mount relative to the endoscope shaft is arranged in the endoscope housing nonrotatably relative thereto.

As mentioned above, this feature has the advantage that the rotational position of the mount relative to the endoscope shaft can be displayed and observed, for example, on the monitor.

It is preferred and advantageous in this context if the aperture is arranged in an intermediate image plane and is shifted together with the eyepiece lens arrangement.

Further advantages are evident from the description below of the appended drawings.

It is understood that the features mentioned above and those yet to be explained below can be used not only in the respective combinations indicated, but also in other combinations or in isolation, without leaving the context of the present invention.

Exemplary embodiments of the invention are shown in the drawings and will be described in more detail hereinafter. In the drawings:

DETAILED DESCRIPTION OF PREFERRED EMBODIMENTS

Figure 1:
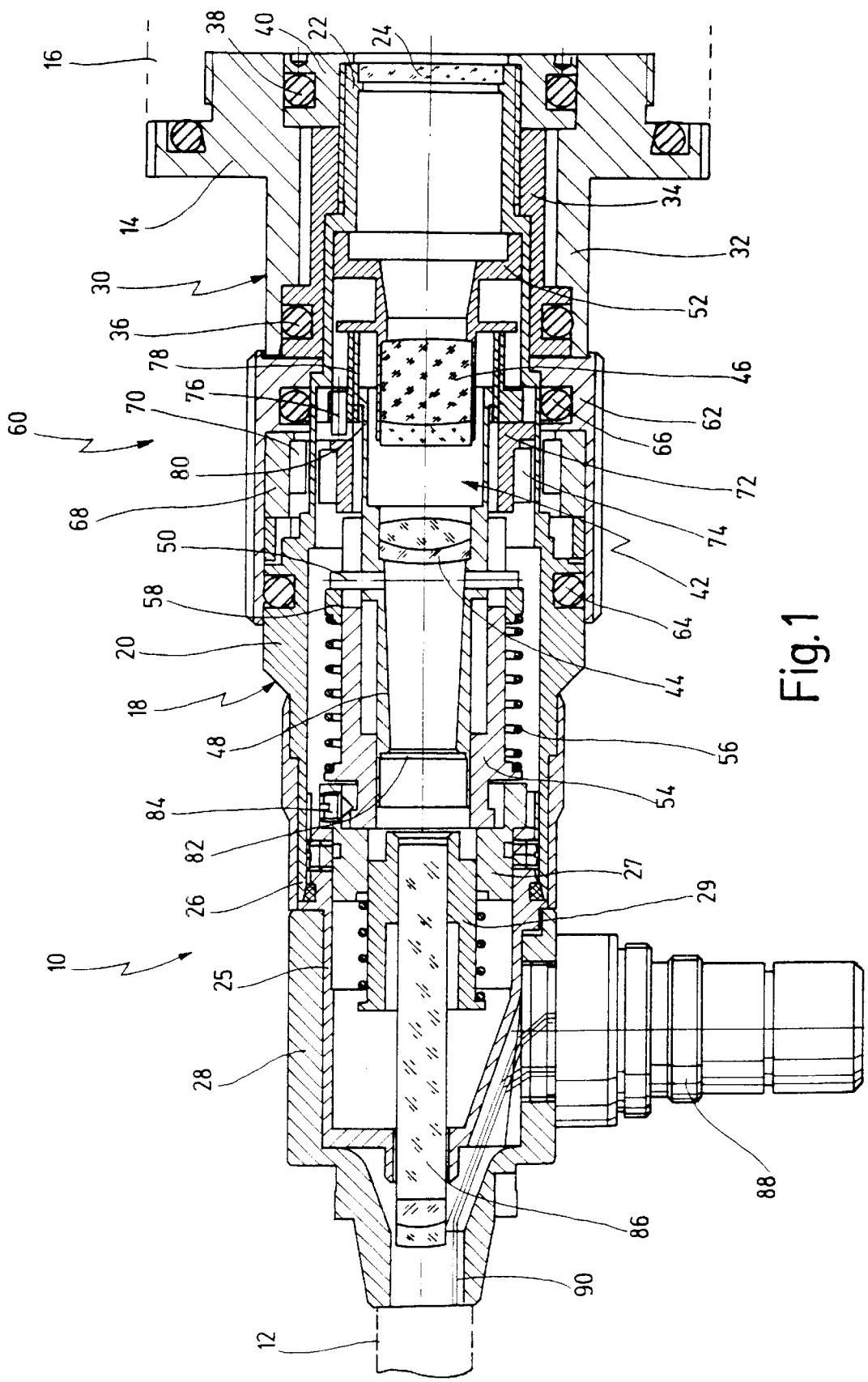
FIG. 1 shows a longitudinal section through an endoscope according to a first exemplary embodiment of the invention.

FIG. 1 shows an endoscope labeled with the general reference character 10. Endoscope 10 is a video endoscope, for example to be used in arthroscopy.

At its distal end, endoscope 10 has an endoscope shaft 12 indicated with broken lines. At its proximal end, endoscope 10 has a mount 14 for attaching an optical imaging device 16, for example a video camera, that is indicated in FIG. 1 with broken lines.

Mount 14 is a C-mount corresponding to DIN 15 735 (Part 2).

Between endoscope shaft 12 and mount 14, endoscope 10 has an endoscope housing 18 whose interior space is hermetically sealed from the outside.

Endoscope housing 18 is nonrotatably joined to endoscope shaft 12.

Endoscope housing 18 is constituted by a substantially cylindrical main housing part 20 that is hermetically sealed at its proximal end 22 by a cover glass 24. Cover glass 24 is, for example, adhesively bonded (using a moisture- and heat-resistant adhesive) or soldered into the opening of main housing part 20 at proximal end 22.

At distal end 26 of main housing part 20, the latter is joined in nonrotatable and hermetically sealed fashion, by way of an adhesively bonded and additionally sealed threaded joint, to a sleeve 25 that in turn adjoins, in nonrotatable and hermetically sealed fashion, the inner tube (not shown in FIG. 1) of the nonrotatable endoscope shaft 12 enclosing lens arrangement 86, for example is soldered thereto. Main housing part 20 could also be configured integrally and continuously up to endoscope 12. Further elements 27, 28, and 29 are arranged in the distal region of endoscope housing 18.

Mount 14 is rotatable, by way of a rotary joint 30, relative to endoscope shaft 12 about the longitudinal axis of endoscope 10. To constitute rotary joint 30, mount 14 is fastened rotatably on the outer side of endoscope housing 18. Mount 14 has a sleeve 32 that at least partially circumferentially surrounds endoscope housing 18 and main housing part 20 at the proximal end. Sleeve 32 is rotatably mounted on an inner sleeve 34 joined immovably to main housing part 20. To ensure that mount 14 is rotatable with respect to endoscope shaft 12 only upon exertion of a defined minimum torque, mount 14 is mounted in frictionally engaged fashion on endoscope housing 18. An O-ring distally received in inner sleeve 34, and an O-ring received in a ring 40, are provided for this purpose at the proximal end of mount 14.

An optically imaging arrangement 42 is arranged in endoscope housing 18. Optically imaging arrangement 42 comprises an eyepiece lens arrangement 44 of endoscope 10 and an objective lens arrangement 46 of optical imaging device 16.

Eyepiece lens arrangement 44 is fastened immovably in an eyepiece mount 48. Eyepiece mount 48 is arranged in endoscope housing 18 nonrotatably, by way of a rotation prevention pin 50, relative to endoscope housing 18 and thus to endoscope shaft 12. Eyepiece lens arrangement 44 is thus also nonrotatable with respect to endoscope shaft 12.

Objective lens arrangement 46 is fastened in endoscope housing 18 in an objective mount 52 that is positionally fixed with respect to endoscope housing 18.

Eyepiece mount 48 is received in axially shiftable fashion in a positionally fixed eyepiece guide 54. Arranged around eyepiece guide 54 is a compression spring 56 that presses, via a ring 58 that is axially shiftable relative to eyepiece guide 54, against rotation prevention pin 50 joined immovably to eyepiece mount 48, and thereby preloads eyepiece mount 48 in the direction toward the proximal end of endoscope 10. Eyepiece mount 48 is thus axially shiftable, whereas objective mount 52 is axially nonshiftable and nonrotatable.

Endoscope 10 moreover has an adjusting device 60 to focus the beam path extending from endoscope shaft 12 to optical imaging device 16, i.e. to focus the image received by optical imaging device 16. As is evident from the description that follows, adjusting device 60 acts from outside, through the sealed housing 18, on optically imaging arrangement 42 in order to positionally displace the latter for focusing.

Adjusting device 60 has an adjusting ring 62 that surrounds the outer side of endoscope housing 18 and is rotatable relative thereto. Adjusting ring 62 is mounted in frictionally engaged fashion on main housing part 20 by way of an O-ring 64 and an O-ring 66, so that in order to rotate adjusting ring 62 on main housing part 20, it is necessary to exert a torque that overcomes the frictional engagement defined by O-rings 64 and 66.

Adjusting device 60 furthermore has an outer ring element 68 arranged around the outer side of endoscope housing 18. Outer ring element 68 is circumferentially continuous, and carries magnets 70, specifically twenty-four such magnets 70, distributed circumferentially on its inner side. Outer ring element 68 constitutes a magnetic return path between the individual magnets 70, i.e. no field lines emerge from the outer side of outer ring element 68. Outer ring element 68 is additionally joined, at its outer side, immovably to adjusting ring 62.

An inner ring element 72, bearing an equal number of magnets 74 lying opposite magnets 70, is arranged inside endoscope housing 18 opposite outer ring element 68. A rotation of outer ring element 68, by rotating adjusting ring 62, causes a rotation of inner ring element 72 in the same direction. The magnetic nonpositive engagement between magnets 70 and 74 acts through housing 18, more precisely through main housing part 20, main housing part 20 being made, for the purpose, of a suitable material.

In order to convert the rotary movement of inner ring element 72 into an axial shift of eyepiece mount 48, inner ring element 72 is nonrotatably joined via a driver pin 76 to a nut 78. Nut 78 in turn is joined, via threads configured on its inner side, to corresponding threads at proximal end 80 of eyepiece mount 48. A rotary movement of inner ring element 72 thus causes eyepiece mount 48, which is nonrotatable because of rotation prevention pin 50, to be shifted axially in eyepiece guide 54 by nut 78, by way of the threaded connection at distal end 80.

In addition, an aperture 82 is immovably mounted in eyepiece mount 48 and is therefore axially shiftable together with eyepiece lens arrangement 44. Also provided are three alignment screws 84 for eyepiece guide 54, of which only one is shown in FIG. 1, with which the assembly made up of eyepiece lens arrangement 44 and aperture 82 can be aligned radially with respect to endoscope shaft 12 in order to correct image location deviations during image transmission.

Also received in endoscope housing 18 is a further lens arrangement 86, constituting a component of the image transmission system of endoscope shaft 12, that is nonrotatable with respect to aperture 82, eyepiece lens arrangement 44, and objective lens arrangement 46.

Endoscope 10 furthermore has a connector 88 for attaching a light guide system, from which light guides 90 lead into endoscope shaft 12 in order to illuminate the inspection field.

The manner of operation of endoscope 10 will now be described. Mount 14 and thus optical imaging device 16 attached thereto can be rotated relative to endoscope shaft 12 and endoscope housing 18 joined nonrotatably thereto. Adjusting ring 62 is rotated for focusing, endoscope housing 18 being held in place for that purpose. A rotation of adjusting ring 62 results, by way of the rotation, associated therewith, of outer ring element 68, in a rotation of inner ring element 72 in the same rotation direction, so that eyepiece lens arrangement 44 is axially shifted relative to objective lens arrangement 46 because of the mechanical threaded connection between inner ring element 72, driver pin 76, nut 78, and proximal end 80 of eyepiece mount 48.

Also applied on aperture 82 on its periphery is a marking, not shown in FIG. 1, which makes it possible to determine the rotational position of mount 14, and thus of optical device 16, relative to endoscope shaft 12, which is nonrotatable with respect to aperture 82. Lens arrangement 86, aperture 82, eyepiece lens arrangement 44, and objective lens arrangement 46 always have the same rotational orientation with respect to one another, regardless of the rotational position of mount 14 relative to endoscope shaft 12.

Figure 2:
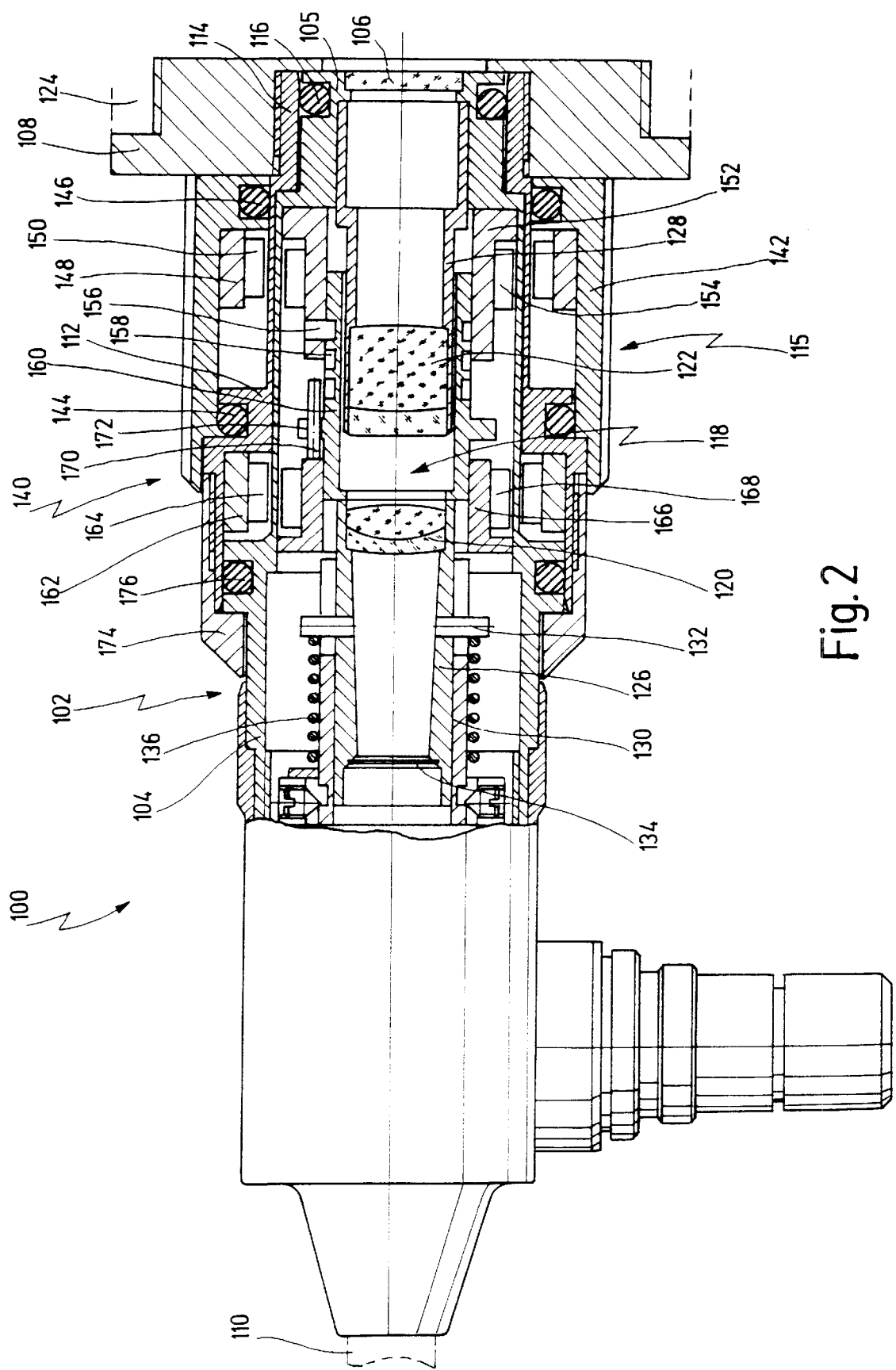
FIG. 2 shows a partial longitudinal section through an endoscope according to a second exemplary embodiment of the invention.

FIG. 2 shows a further exemplary embodiment of an endoscope, labeled with the reference character 100. Unless otherwise evident from the description that follows, endoscope 100 corresponds to endoscope 10 in FIG. 1 in terms of design and function.

Endoscope 100 has an endoscope housing 102 that is constituted by a main housing part 104 that is once again sealed hermetically at the proximal end by a cover glass 106.

A mount 108 at the proximal end of endoscope 100 is mounted rotatably on endoscope housing 102 relative to an endoscope shaft 100 that is immovably joined to endoscope housing 102. Mount 108 is joined immovably to a sleeve-shaped joining element 112, mount 108 being rotatably mounted, via proximal end 114 of joining element 112, on proximal end 105 of main housing part 104 to constitute a rotary joint 115. O-rings 116 and 176 provide for a defined torque upon rotation of mount 108 with respect to endoscope housing 102.

An optically imaging arrangement 118, comprising an eyepiece lens arrangement 120 of endoscope 100 and an objective lens arrangement 122 of an optical imaging device 124 that can be attached to mount 108, is received in endoscope housing 102.

Eyepiece lens arrangement 120 is immovably mounted in an eyepiece mount 126, while objective lens arrangement 122 is immovably mounted in an objective mount 128. Objective mount 128 is received, nonrotatably and axially nonshiftably, in endoscope housing 102.

Eyepiece mount 126, on the other hand, is received in axially shiftable fashion in an eyepiece guide 130, but is arranged nonrotatably in endoscope housing 102 as a result of a rotation prevention pin 132. An aperture 134 is also mounted immovably in eyepiece mount 126. A compression spring 136 is arranged around eyepiece guide 130 and preloads eyepiece mount, via rotation prevention pin 132, toward the proximal end of endoscope 100.

Endoscope 100 has an adjusting device 140 for focusing the image transmitted from endoscope 110 into optical imaging device 124.

Adjusting device 140 has an adjusting ring 142. Adjusting ring 142 is rotatable relative to mount 108 in order to positionally displace optically imaging arrangement 118. For that purpose, adjusting ring 142 is mounted rotatably around joining element 112 that is joined immovably to mount 108. An O-ring 144 carried by joining element 112, and an O-ring 146 carried by adjusting ring 142, effect a frictionally engaged connection between adjusting ring 142 and joining element 112, and by way of the latter to mount 108, so that adjusting ring 142 can be rotated with respect to mount 108 only by exerting a specific torque. Adjusting ring 142 is, of course, also rotatable with respect to endoscope housing 102.

Adjusting device 140 has a first outer ring element 148 that is arranged circumferentially on the outer side of endoscope housing 102 and of joining element 112. First outer ring element 148 carries on its inner side, i.e. on the side facing toward joining element 112, magnets 150 that are arranged in circumferentially distributed fashion on the inner side of first outer ring element 148.

The outer side of outer ring element 148 is immovably joined to adjusting ring 142 on its inner side.

Arranged opposite first outer ring element 148, inside main housing part 104, is a first inner ring element 152 that carries on its outer side magnets 154 that lie radially opposite magnets 150. Magnets 150 and 154 coact, through joining element 112 and main housing part 104, via a magnetic nonpositive engagement.

Mounted on first inner ring element 152 is a pin 156 that engages into a helical groove 158 that is configured in a slider 160 that is mounted rotatably about objective mount 128. Eyepiece mount 126 is braced with its proximal end against the distal end of slider 160. Compression spring 136 preloads eyepiece 126 against slider 160.

Slider 160 is mounted both rotatably and axially shiftably with respect to eyepiece mount 128. First inner ring element 152 is mounted rotatably, but in axially stationary fashion, in endoscope housing 102.

Adjusting device 140 has a second outer ring element 162 that is arranged circumferentially around endoscope housing 102 on its outer side and is rotatable relative to the latter about the longitudinal axis of endoscope 100. Second outer ring element 162 is immovably joined to the distal end of joining element 112 which, as already mentioned, is joined nonrotatably to mount 108. The assembly made up of second outer ring element 162, joining element 112, and mount 108 thus constitutes an immovably interconnected unit that is rotatable with respect to endoscope housing 102.

Second outer ring element 162 once again carries, on its inner side, magnets 164 arranged in circumferentially distributed fashion. Arranged on the inner side of endoscope housing 102 is a second inner ring element 166 that lies radially opposite second outer ring element 162 and is mounted rotatably in the interior space of endoscope housing 102. Second inner ring element 166 carries on its outer side magnets 168, radially opposite magnets 164, that coact with magnets 164. "Coact" once again means that a rotation of second outer ring element 162 results in a rotation of second inner ring element 166 in the same direction.

Second inner ring element 166 is received in axially nonshiftable fashion in endoscope housing 102. Second inner ring element 166 partially surrounds slider 160, slider 160 being axially shiftable relative to second inner ring element 166.

A driver pin 170 joined immovably to second inner ring element 166 coacts with a groove 172 configured on slider 160 in such a way that second inner ring element 166 and slider 160 can only rotate together, in either direction, in endoscope housing 102. Inner ring element 166 and slider 160 are thus nonrotatable relative to one another.

Also joined immovably to joining part 112 at its distal end is a bearing sleeve 174 that can thus rotate, together with joining element 112 and mount 108, around endoscope housing 102 about the longitudinal axis of endoscope 100. By way of an O-ring 176 together with O-ring 116, a minimum torque for rotation of mount 108 and thus of optical imaging device 124 relative to endoscope housing 102 and thus to endoscope shaft 110 is defined by frictional engagement.

The manner of operation of endoscope 100 will now be explained. In this context, endoscope housing 102 with endoscope shaft 110 will be considered as a stationary reference system.

If mount 108 is held in place in one hand, it is possible, with the thumb and the index or middle finger, to rotate adjusting ring 142 relative to mount 108 and relative to optical imaging device 124 in order to focus or positionally displace optical imaging arrangement 118. A rotation of adjusting ring 142 causes a rotation of first outer ring element 148 and of magnets 150 joined immovably thereto. Magnets 150 of first outer ring element 148, coacting magnetically with magnets 154 of first inner ring element 152 by way of joining element 112 and main housing part 104, cause a rotary movement of first inner ring element 152 in the same direction as first outer ring element 148.

Since mount 108 is being held in place, second outer ring element 162, and therefore also second inner ring element 166 that is magnetically coupled to it, are stationary. First outer ring element 148 and first inner ring element 152 thus perform a relative rotation with respect to second outer ring element 162 and second inner ring element 166. Slider 160 is also held nonrotatably, by way of driver pin 170, along with second inner ring element 166, so the result of the rotary movement of first inner ring element 152 is that pin 156 circulates in helical groove 158 and thereby shifts slider 160 toward the proximal end of endoscope 100. Since compression spring 136 is pushing eyepiece mount 126 toward slider 160, eyepiece mount 126 follows the axial movement of slider 160. A rotation of adjusting ring 142 in the opposite direction causes eyepiece lens arrangement 120 to be correspondingly shifted toward the distal end of endoscope 100 against the force of the compression spring. It is thus possible to focus the image by rotating adjusting ring 142 while mount 108 and optical imaging device 124 are held in place.

If, on the other hand, all that is necessary is to change the rotational position of optical imaging device 124 relative to endoscope shaft 110, with no need for focusing to be performed, mount 108 is simply rotated while adjusting ring 142 is not held. In this case second outer ring element 162 rotates, and by way of the magnetic coupling, second inner ring element 166 rotates along with it, also causing slider 160 to rotate by way of driver pin 170. Since adjusting ring 142 is joined to mount 108 in frictionally engaged fashion via O-rings 144 and 146, adjusting ring 142 also rotates along with mount 108. As a result, first outer ring element 148, and first inner ring element 152 magnetically coupled to it, also rotate. First outer ring element 148 and second outer ring element 162 thus do not perform any relative rotation with respect to each other, but rather rotate together around endoscope housing 102. Pin 156 on first inner ring element 152 thus also rotates, together with slider 160 that is rotationally driven by second inner ring element 166 by way of driver pin 170, so that pin 156 does not circulate in helical groove 158. There is therefore no axial shifting of eyepiece mount 126 or of eyepiece lens arrangement 120.

What is claimed is:

1. An endoscope, comprising
   an endoscope shaft,
   a mount for attaching an optical imaging device,
   and endoscope housing arranged between said endoscope shaft and said mount,
   an optical imaging arrangement disposed inside said endoscope housing and being at least partially positionally displaceable,
   an adjusting device for positionally displacing said optical imaging arrangement for focusing the image transmission,
   said mount being rotatable relative to said endoscope shaft via a rotary joint about a longitudinal axis of said endoscope,
   wherein said endoscope housing is configured in continuously hermetically sealed fashion and said rotary joint is arranged outside said endoscope housing and is configured at said mount.

2. The endoscope of claim 1, wherein said rotary joint is arranged in the region of the proximal end of said endoscope housing.

3. The endoscope of claim 1, wherein said mount has at its distal end a sleeve that is arranged circumferentially and mounted rotatably on said endoscope housing.

4. The endoscope of claim 1, wherein said endoscope housing is joined nonrotatably to said endoscope shaft.

5. The endoscope of claim 1, wherein said adjusting device acts on said optical imaging arrangement from outside through said sealed endoscope housing.

6. The endoscope of claim 1, wherein said adjusting device acts of said optical imaging arrangement via a magnetic nonpositive engagement.

7. The endoscope of claim 1, wherein said adjusting device has an adjusting ring that is arranged around the outer side of said endoscope housing and is rotatable relative to said endoscope shaft for positional displacement of at least a portion of said optical imaging arrangement.

8. The endoscope of claim 1, wherein said adjusting device has an adjusting ring that is rotatable relative to said mount for positional displacement of at least a portion of said optical imaging arrangement.

9. The endoscope of claim 1, wherein said adjusting device has at least one outer ring element, arranged rotatably around the outer side of said endoscope housing, that carries at least one magnet, and at least one rotatable inner ring element, arranged inside said endoscope housing, that also carries at least one magnet, such that a rotation of said outer ring element moves said inner ring element, and the movement of said inner ring element serves to positionally displace at least a portion of said optical imaging arrangement.

10. The endoscope of claim 9, wherein said movement of said inner ring element is converted via a mechanical connection into an axial movement of at least a porton of said optical imaging arrangement.

11. The endoscope of claim 1, wherein said adjusting device has two outer ring elements, arranged around said outer side of said endoscope housing, that each carry at least one magnet, and two inner ring elements, arranged inside said endoscope housing, that also each carry at least one magnet, such that a rotary movement of said outer ring elements moves the respective associated inner ring element, and such that a rotation of said one outer ring element relative to said other outer ring element effects a positonal displacement of at least a portion of said optical imaging arrangement.

12. The endoscope of claim 11, wherein said one outer ring element is joined nonrotatably to said mount, and said other outer ring element is rotatable relative to the latter.

13. The endoscope of claim 12, wherein said outer ring element that is not joined nonrotatably to said mount is joined in frictionally engaged fashion to said mount.

14. The endoscope of claim 1, wherein said optical imaging arrangement comprises an axially shiftable eyepiece lens arrangement of said endoscope and an objective lens arrangement of said optical imaging device; and for focusing said eyepiece lens arrangement is shifted by way of said adjusting device.

15. The endoscope of claim 1, wherein said optical imaging arrangement is arranged nonrotatably in said endoscope housing.

16. The endoscope of claim 1, wherein an aperture that has a marking for determining the rotational position of said mount relative to said endoscope shaft is arranged in said endoscope housing nonrotatably relative thereto.

17. The endoscope of claim 16, wherein said optical imaging arrangement comprises an axially shiftable eyepiece lens arrangement, and wherein said aperture is arranged in an intermediate image plane and is shifted together with said eyepiece lens arrangement.

18. The endoscope of claim 1, wherein said optical imaging device comprises a video camera.

19. An endoscope, comprising
an endoscope shaft,
a mount for attaching an optical imaging device,
and endoscope housing arranged between said endoscope shaft and said mount,
an optical imaging arrangement disposed inside said endoscope housing and being at least partially positionally displaceable,
an adjusting device for positionally displacing said optical imaging arrangement for focusing the image transmission,
  wherein said adjusting device has two outer ring elements, arranged around said outer side of said endoscope housing, that each carry at least one magnet, and two inner ring elements, arranged inside said endoscope housing, that also each carry at least one magnet, such that a rotary movement of said outer ring elements moves the respective associated inner ring element, and such that a rotation of said one outer ring element relative to said other outer ring element effects a positonal displacement of at least a portion of said optical imaging arrangement, and
  wherein said one outer ring element is joined nonrotatably to said mount, and said other outer ring element is rotatable relative to the latter, said mount being rotatable relative to said endoscope shaft via a rotary joint about a longitudinal axis of said endoscope,
wherein said endoscope housing is configured in continuously hermetically sealed fashion and said rotary joint is arranged outside said endoscope housing and is configured at said mount.

20. The endoscope of claim 19, wherein said outer ring element that is not joined nonrotatably to said mount is joined in frictionally engaged fashion to said mount.

* * * * *